United States Patent
Naik et al.

(10) Patent No.: US 9,045,397 B2
(45) Date of Patent: Jun. 2, 2015

(54) PROCESSES FOR MAKING MAGNOLOL ANALOGS

(75) Inventors: Ramesh Naik, Karnataka (IN); Sanju Walikar, Karnataka (IN); Govindarajalu Jeyaraman, Karnataka (JP); Koottungalmadhom Ramaswamy Ranganathan, Karnataka (JP)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/365,676

(22) PCT Filed: Dec. 20, 2011

(86) PCT No.: PCT/US2011/066053
§ 371 (c)(1),
(2), (4) Date: Jun. 16, 2014

(87) PCT Pub. No.: WO2013/095364
PCT Pub. Date: Jun. 27, 2013

(65) Prior Publication Data
US 2014/0343328 A1   Nov. 20, 2014

(51) Int. Cl.
| | |
|---|---|
| *C07C 37/50* | (2006.01) |
| *C07C 37/00* | (2006.01) |
| *C07C 37/055* | (2006.01) |
| *C07C 41/16* | (2006.01) |
| *C07C 41/18* | (2006.01) |
| *C07C 45/46* | (2006.01) |

(52) U.S. Cl.
CPC .............. *C07C 37/50* (2013.01); *C07C 37/003* (2013.01); *C07C 37/055* (2013.01); *C07C 41/16* (2013.01); *C07C 41/18* (2013.01); *C07C 45/46* (2013.01); *C07C 2101/16* (2013.01)

(58) Field of Classification Search
CPC .............................. C07C 37/50; C07C 37/003
USPC .................................................. 568/730, 799
See application file for complete search history.

(56) References Cited

U.S. PATENT DOCUMENTS

| | | |
|---|---|---|
| 7,608,741 B2 | 10/2009 | Kim et al. |
| 2006/0140880 A1 | 6/2006 | Subramanyam et al. |
| 2008/0039643 A1 | 2/2008 | Vass et al. |
| 2009/0149402 A1 | 6/2009 | Miyagi et al. |
| 2010/0056463 A1 | 3/2010 | Raederstorff et al. |

FOREIGN PATENT DOCUMENTS

| | | |
|---|---|---|
| CN | 1270168 | 10/2000 |
| CN | 101293816 | 10/2008 |
| JP | 2004292392 | 10/2004 |
| JP | 2007326798 | 12/2007 |
| WO | WO0185116 | 11/2001 |
| WO | WO 2010/073124 | 7/2010 |
| WO | WO2011106003 | 9/2011 |
| WO | WO2011106492 | 9/2011 |
| WO | WO2011106493 | 9/2011 |

OTHER PUBLICATIONS

International Search Report and the Written Opinion issued in International Application PCT/US2011/066053 mailed Jun. 28, 2012.
Krishnaswamy, Resonance, 2004, 9(2):26-38, pp. 27-28.
Sobrinho E.V. et al., "Thermodynamic Analysis of Phenol Acylation with Acetic Acid," J. Braz., Chem. Soc., 1998, 9(3):225-230.

*Primary Examiner* — Brian J Davis
(74) *Attorney, Agent, or Firm* — Anne Louise St. Martin

(57) ABSTRACT

Described herein are high yield methods for making magnolol analogs which are 5,5'-dialkyl-bi-phenyl-2,2'-diols.

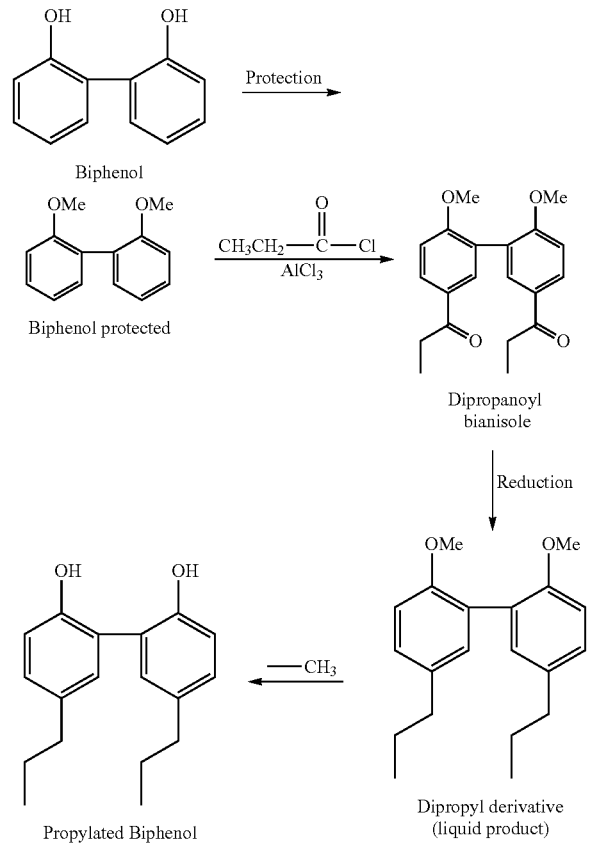

10 Claims, No Drawings

PROCESSES FOR MAKING MAGNOLOL ANALOGS

CROSS-REFERENCE TO RELATED PATENT APPLICATIONS

The present application is a U.S. national stage entry under 35 U.S.C. §371 of Patent Cooperation Treaty Patent Application No. PCT/US2011/66053, filed Dec. 20, 2011, the entirety of which is incorporated herein by reference.

BACKGROUND

There is a need for safe, effective antibacterial and anti-inflammatory agents for use in oral care compositions. Magnolia extract is known to contain compounds having antibacterial and/or anti-inflammatory properties, and such compounds have been the focus of considerable interest for use in oral care compositions. The use of such compounds in oral care compositions is described, for example, in WO2001/085116, WO 2011/106492 and WO 2011/106493, the contents of which application are incorporated herein by reference. Methods of synthesizing magnolol are disclosed, e,g, in WO 2011/106003. Synthetic non-natural analogs of various components of magnolia extract are also known to have antibacterial activity, but the compounds are in some cases expensive to synthesize.

Magnolol analogs having lower alkyl in place of allyl are of particular interest, as are compounds wherein the alkyl or allyl side chains are ortho rather than para to the hydoxy goups (isomanolols). Tetrahydro-magnolol, (5,5'-dipropyl-biphenyl-2,2'-diol) is a broad spectrum antibacterial and anti-inflammatory agent with potential applications in oral care and personal care products. It has advantages over magnolol, e.g. in that it does not stain toothbrush bristles when used as an antibacterial/anti-inflammatory agent in a toothpaste. Existing synthetic methods for making magnolol derivatives, however, involve costly reagents and yields are low. There is a need for cheaper, higher yield synthetic procedures to make magnolol derivatives.

SUMMARY

Previous synthetic approaches to making magnolol generally start with bromination of biphenyl-2,2'-diol, to get the 5,5'-dibromo-biphenyl-2,2'-diol, followed by O-protection, with methyl or other O-protecting group, reaction with allyl bromide to get the magnolol in protected form, deprotection to get magnolol, which can then be hydrogenated to obtain propyl magnolol. Analogous compounds are made analogously. We have found that on scale up, the step of O-protecting the 5,5'-dibromo-biphenyl-2,2'-diol is inefficient and slow. We have found that carrying out the O-protection step before the bromination step results in a more efficient reaction and higher yields.

The deprotection step is another expensive and yield limiting step in the existing processes. The methods reported for demethylation are often costly, and require sometimes very low temperatures (−78° C. using $BBr_3$) and sometimes reflux conditions. The reaction mixture is always difficult to separate and purify which results in low yield of magnolol. We have found that the use of an aluminium chloride/thiourea complex for deprotection does not require extreme temperatures or expensive reagents and results in high yields.

Finally, we avoid the need for a bromination step or a hydrogenation step or a difficult separation of alkyl analogs of magnolol from magnolol by introducing the alkyl group by Friedel-Crafts acylation of 2,2'-bianisole followed by Clemmensen reduction of the alkionyl derivative.

The invention thus provides a simple, relatively high yield synthesis for 5,5'-dialkyl-biphenyl-2,2'-diols, comprising
(i) methylating biphenyl-2,2'-diol using dimethyl sulfate, to obtain 2,2'-dimethoxy-biphenyl;
(ii) acylating the 2,2'-dimethoxy-biphenyl with alkionyl halide, for example propionyl chloride, to obtain the corresponding 2,2'-dimethoxy-5,5'-dialkionyl-biphenyl;
(iii) reducing the 2,2'-dimethoxy-5,5'-dialkionyl-biphenyl to obtain 2,2'-dimethoxy-5,5'-dialkyl-biphenyl;
(iv) demethylating the 2,2'-dimethoxy-5,5'-dipropyl-biphenyl by reaction with aluminium chloride and thiourea; and
(v) recovering the 5,5'-dialkyl-biphenyl-2,2'-diol thus obtained;
wherein "alk" or "alkyl" refers to linear, branched or cyclic $C_{2-10}$ alkyl, for example selected from n-propyl, isopropyl, n-butyl, and isobutyl, e.g., n-propyl.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The invention thus provides a method (Method 1) for making 5,5'-dialkyl-biphenyl-2,2'-diols, for example 5,5'-dipropyl-biphenyl-2,2'-diol, comprising
(i) methylating biphenyl-2,2'-diol using dimethyl sulfate, to obtain 2,2'-dimethoxy-biphenyl;
(ii) acylating the 2,2'-dimethoxy-biphenyl with alkionyl halide to obtain 2,2'-dimethoxy-5,5'-dialkionyl-biphenyl;
(iii) reducing the 2,2'-dimethoxy-5,5'-dialkionyl-biphenyl to obtain 2,2'-dimethoxy-5,5'-dialkyl-biphenyl;
(iv) demethylating the 2,2'-dimethoxy-5,5'-dialkyl-biphenyl by reaction with aluminium chloride and thiourea; and
(v) recovering the 5,5'-dialkyl-biphenyl-2,2'-diol thus obtained;
e.g., wherein "alk" or "alkyl" refers to linear, branched or cyclic $C_{2-10}$ alkyl, for example selected from n-propyl, isopropyl, n-butyl, and isobutyl, e.g., n-propyl.
1.1. Method 1 wherein step (i) is carried out in aqueous media in presence of an inorganic base, e.g., sodium hydroxide or potassium hydroxide.
1.2. Any of the foregoing methods wherein step (ii) is carried out in an apolar aprotic solvent, e.g., ethylene dichloride, in the presence of an aluminum chloride catalyst.
1.3. Any of the foregoing methods wherein step (iii) is carried out in the presence of heat, a strong acid, e.g., HCl, and a zinc catalyst.
1.4. Any of the foregoing methods wherein step (iv) is carried out at temperatures between 30° C. and 60° C.
1.5. Any of the foregoing methods wherein the product is 5,5'-dipropyl-biphenyl-2,2'-diol, comprising
(i) methylating biphenyl-2,2'-diol using dimethyl sulfate, to obtain 2,2'-dimethoxy-biphenyl;
(ii) acylating the 2,2'-dimethoxy-biphenyl with propionyl chloride to obtain 2,2'-dimethoxy-5,5'-dipropionyl-biphenyl;

(iii) reducing the 2,2'-dimethoxy-5,5'-dipropionyl-biphenyl to obtain 2,2'-dimethoxy-5,5'-dipropyl-biphenyl;
(iv) demethylating the 2,2'-dimethoxy-5,5'-dipropyl-biphenyl by reaction with aluminium chloride and thiourea; and
(v) recovering the 5,5'-dipropyl-biphenyl-2,2'-diol thus obtained.

The reaction scheme is as follows for 5,5'-dipropyl-biphenyl-2,2'-diol; other 5,5'-dialkyl-biphenyl-2,2'-diols are made analogously using the corresponding alkionyl halides in place of propionyl chloride:

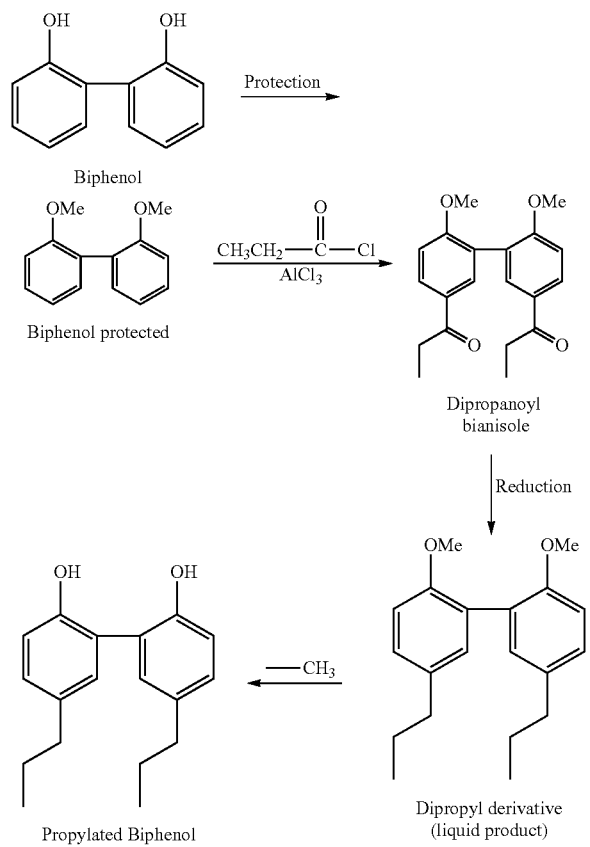

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls Unless otherwise specified, all percentages and amounts expressed herein and elsewhere in the specification should be understood to refer to percentages by weight. The amounts given are based on the active weight of the material.

EXAMPLE

Example 1

Synthesis of Tetrahydro-Magnolol
(5,5'-dipropyl-biphenyl-2,2'-diol)

Protection: Biphenol is reacted in sodium hydroxide with sodium sulfate for 1-2 hours. Solid is separated, washed with water and dried at 60-65 ° C.

Acylation: Combine propionyl chloride with anhydrous aluminum chloride in 1,2-dichloroethane. Add bianisole at room temperature and allow to stir for 4-6 hours. Quench in diluted hydrochloric acid and separate organic layer. Remove solvent via distillation and crystallize from methanol.

Reduction: Reflux 3-5 hours the 4,4'-dipropionyl 2,2'-bianisole in hydrochloric acid with zinc powder. Remove methanol and add ethyl acetate with stirring. Remove zinc by filtration and solvent by distillation.

De-methylation: Add the product of the previous step to a mixture of aluminum chloride, thiourea and 1,2-dichloroethane slowly over 3 hours at 50° C. Maintain temperature and stirring for an additional 3-4 hours. Cool reaction and add to hydrochloric acid and separate phases. Add organic layer to charcoal, filter and distill solvent to recover title compound.

The overall yield is about 55%, with a purity of greater than 98%.

The invention claimed is:

1. A method for making 5,5'-dialkyl-biphenyl-2,2'-diols, comprising the following steps:
   (i) methylating biphenyl-2,2'-diol using dimethyl sulfate, to obtain 2,2'-dimethoxy-biphenyl;
   (ii) acylating the 2,2'-dimethoxy-biphenyl with an alkionyl chloride to obtain 2,2'-dimethoxy-5,5'-dialkionyl-biphenyl;
   (iii) reducing the 2,2'-dimethoxy-5,5'-dialkionyl-biphenyl to obtain 2,2'-dimethoxy-5,5'-dialkyl-biphenyl;
   (iv) demethylating the 2,2'-dimethoxy-5,5'-dialkyl-biphenyl by reaction with aluminium chloride and thiourea; and
   (v) recovering the 5,5'-dialkyl-biphenyl-2,2'-diol thus obtained.

2. The method of claim 1 wherein step (i) is carried out in aqueous media in the presence of an inorganic base.

3. The method of claim 1 wherein step (ii) is carried out in an apolar aprotic solvent in the presence of aluminum chloride.

4. The method of claim 1 wherein step (iii) is carried out in the presence of heat, a strong acid, and a zinc catalyst.

5. The method of claim 1 wherein step (iv) is carried out at temperatures between 30° C. and 60° C.

6. The method of claim 1 wherein "alk" or "alkyl" refers to linear, branched or cyclic $C_{2-10}$ alkyl.

7. The method of claim 1 wherein the product is 5,5'-dipropyl-biphenyl-2,2'-diol, comprising the following steps:
   (i) methylating biphenyl-2,2'-diol using dimethyl sulfate, to obtain 2,2'-dimethoxy-biphenyl;
   (ii) acylating the 2,2'-dimethoxy-biphenyl with propionyl chloride to obtain 2,2'-dimethoxy-5,5'-dipropionyl-biphenyl;
   (iii) reducing the 2,2'-dimethoxy-5,5'-dipropionyl-biphenyl to obtain 2,2'-dimethoxy-5,5'-dipropyl-biphenyl;
   (iv) demethylating the 2,2'-dimethoxy-5,5'-dipropyl-biphenyl by reaction with aluminium chloride and thiourea; and
   (v) recovering the 5,5'-dipropyl-biphenyl-2,2'-diol thus obtained.

8. The method of claim 2 wherein step (i) is carried out in aqueous media in the presence of sodium hydroxide.

9. The method of claim 2 wherein step (i) is carried out in aqueous media in the presence of potassium hydroxide.

10. The method of claim 1 wherein step (iii) is carried out in the presence of heat, HCl, and a zinc catalyst.

* * * * *